(12) United States Patent
Müller

(10) Patent No.: US 7,311,439 B2
(45) Date of Patent: Dec. 25, 2007

(54) COOLING SYSTEM AND METHOD TO COOL A GANTRY

(75) Inventor: Hans-Jürgen Müller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 252 days.

(21) Appl. No.: 10/803,242

(22) Filed: Mar. 18, 2004

(65) Prior Publication Data

US 2004/0202287 A1    Oct. 14, 2004

(30) Foreign Application Priority Data

Mar. 19, 2003  (DE)  ................................. 103 12 253

(51) Int. Cl.
*H01J 35/10* (2006.01)
*H01G 1/60* (2006.01)

(52) U.S. Cl. ............................. 378/199; 378/4; 378/15

(58) Field of Classification Search .................... 378/4, 378/15, 141, 199, 200
See application file for complete search history.

(56) References Cited

U.S. PATENT DOCUMENTS

| | | | | |
|---|---|---|---|---|
| 3,151,471 A | * | 10/1964 | Weil | 62/332 |
| 4,115,697 A | * | 9/1978 | Hounsfield et al. | 378/15 |
| 4,264,282 A | * | 4/1981 | Crago | 417/243 |
| 4,696,167 A | * | 9/1987 | Matsui et al. | 62/180 |
| 5,012,505 A | | 4/1991 | Zupancic et al. | |
| 5,761,269 A | * | 6/1998 | Sugihara et al. | 378/199 |
| 6,129,524 A | * | 10/2000 | Woollenweber et al. | 417/366 |
| 6,412,979 B1 | * | 7/2002 | Hell et al. | 378/200 |

FOREIGN PATENT DOCUMENTS

DE        199 45 413 A1     4/2001

* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

A cooling system is provided for components of a computer tomography system that are arranged in a gantry housing. The cooling system includes a cooled air feed device with an air compressor and connected streaming elements that are arranged and/or fashioned such that compressed air flows onto the components to be cooled. Moreover, a corresponding method is provided for cooling the components of a computer tomography system arranged in a gantry housing.

15 Claims, 4 Drawing Sheets

FIG 2
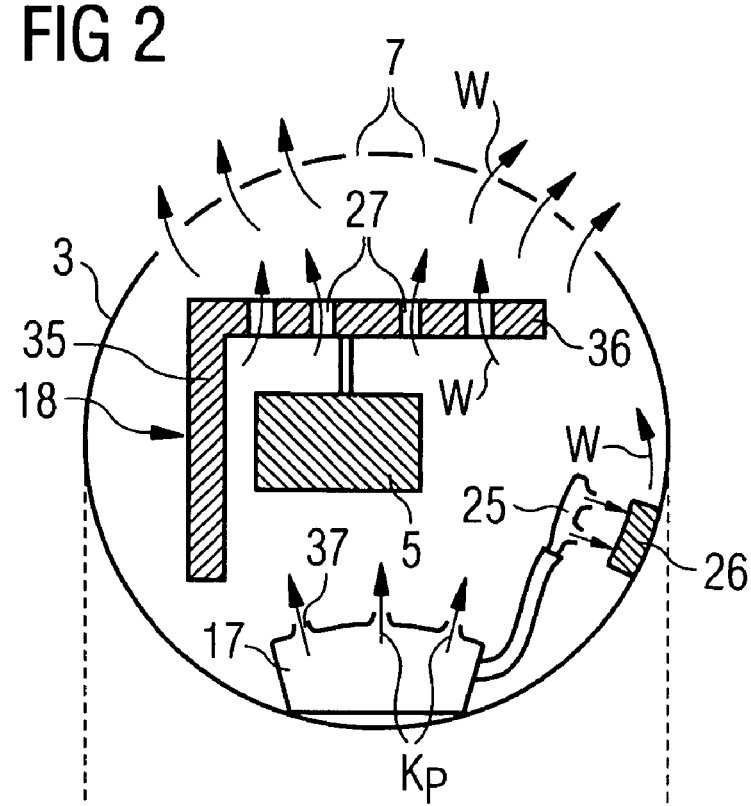
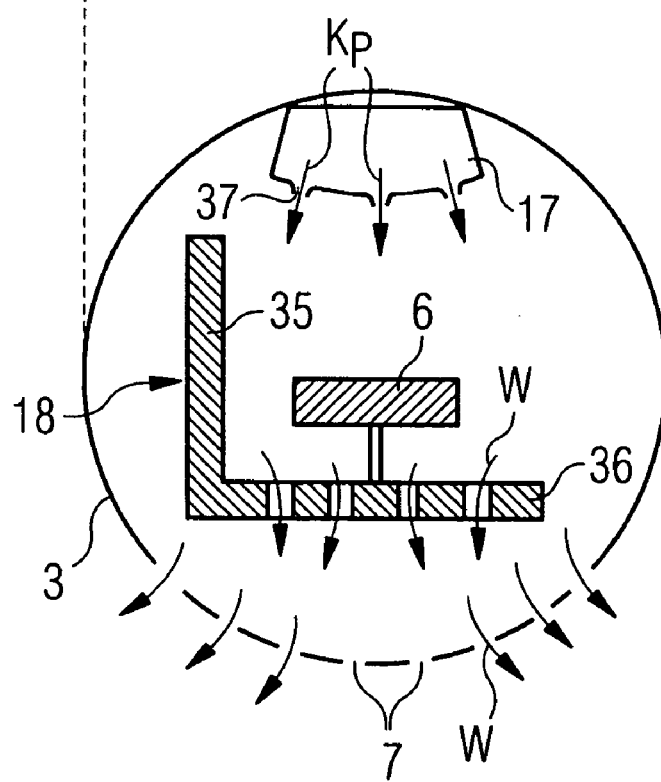

FIG 4
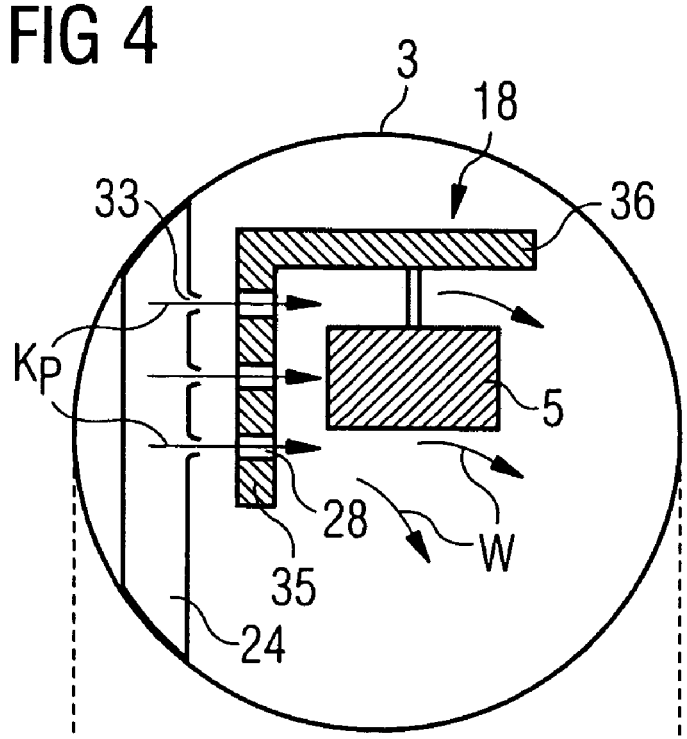
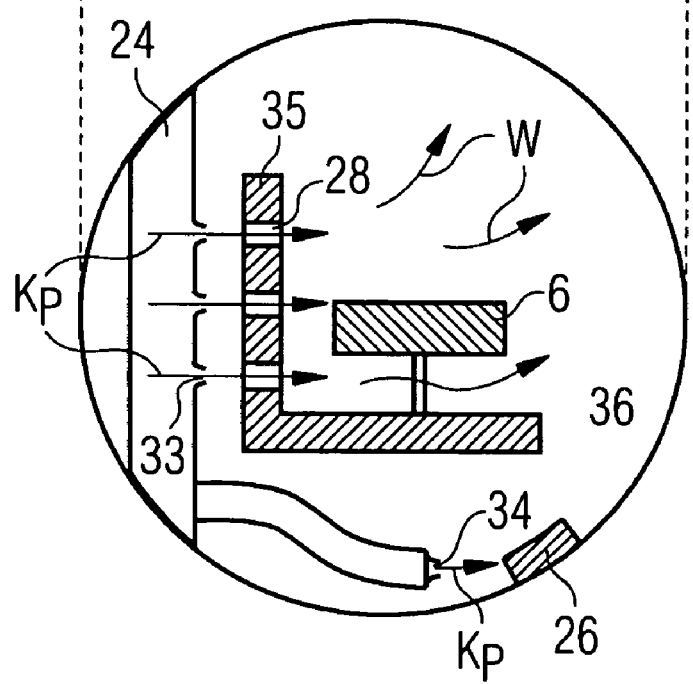

COOLING SYSTEM AND METHOD TO COOL A GANTRY

BACKGROUND OF THE INVENTION

1. Field of the Invention

The present invention relates generally to a. a cooling system to cool components of a computer tomography system arranged in a gantry housing. Moreover, the invention concerns a corresponding method to cool such components.

2. Description of the Related Art

In computer tomography systems, three-dimensional slice images of the inside of an examination subject are generated with the aid of an x-ray method. For this, two-dimensional x-ray slice images from which a three-dimensional slice image is reconstructed are generated by means of a scanning unit—generally called a gantry—which comprises an x-ray source (normally rotating around the acquisition subject) and an image acquisition system. The gantry is hereby typically located in a gantry housing which is annularly arranged around an examination subject acquisition space.

A fundamental problem in all x-ray systems is that 99% of the electrical energy used in the generation of the x-ray radiation in the x-ray source is transduced into heat energy. This heat that is incidental in the operation of the x-ray source must be dissipated in order to be able to operate over a longer period of time without overheating. This is in particular necessary when high x-ray capacities are required. As explained above, it is additionally aggravating in computer tomography systems that the x-ray source normally permanently rotates in the gantry housing around the examination subject acquisition space during a radiological acquisition. Due to this continuous rotation movement, the extremely high temperatures and the narrowness of the inner space of the gantry housing, the dissipation of the heat incidental in the operation of the x-ray source has proven to be complex and problematic.

The cooling systems previously used in such computer tomography systems normally comprise a plurality of heat exchangers that are installed inside the gantry housing. In order to dissipate the heat incidental on the rotating x-ray source from the gantry and from the inside of the gantry housing with optimal efficiency, conventionally a rotating heat exchanger is mounted in direct proximity to the x-ray source. This first heat exchanger delivers the heat to the air surrounding the gantry in the gantry housing. The heated air around the gantry can, for example, be cooled by a second heat exchanger which dissipates the heat acquired from the air to a cooling system outside of the gantry housing. German patent document DE 199 45 413 A1 shows a computer tomography system in which the second heat exchanger is thereby arranged stationary in the gantry housing relative to the x-ray radiator. The heat absorbed during the operation is dissipated via coolant lines (arranged in the second heat exchanger) to a cooling system outside of the gantry housing. German patent document DE 198 45 756 A1 offers an alternative. In the computer tomography system shown there, the second heat exchanger is arranged rotating in the gantry housing with the gantry. The dissipation of the heat ensues during the idle periods of the gantry between two measurements, in that the second heat exchanger is coupled by means of a fast coupling with a water cooling circuit arranged outside of the gantry housing.

It has proven to be disadvantageous in the cited cooling systems that a plurality of precise mechanical and electrical components are required that, due to their function, tend to wear out and must be correspondingly maintained. A further disadvantage is that the gantry housing must be correspondingly voluminously dimensioned based on the size of the required heat exchanger. Quite good cooling capacities can be achieved with a sufficiently large heat exchanger. However, it is disadvantageous that the cooling of the coolant is possible only given sufficient idle periods for the device. For the rest, the necessary coupling to an external coolant circuit complicates the assembly in which the gantry housing is positioned since a connection must be made between a stationary part of the computer tomography system such the parts can be pivoted.

It is desired so have such an assembly because by pivoting the gantry housing or, respectively, the gantry, a tilting of the image plane relative to the examination subject can be achieved in order to achieve, for example, a slice guide that is parallel to the subject surfaces. For example, arbitrary coronary slices can be created in this manner.

SUMMARY OF THE INVENTION

The present invention provides a simply assembled, cost-effective cooling system and method which requires less space in the gantry housing.

A cooled air supply device is used to cool the components in the gantry housing in order to guide compressed air via streaming elements (for example via suitable nozzles) into the gantry housing and directly to the components to be cooled. A method is also provided of cooling the computer tomography apparatus in the annular gantry housing by directing compressed air into the components to be cooled.

A particular advantage of fashioning of the cooling system as a cooled compressed air system is that very little space is required in the gantry housing. A cost-saving design of a smaller gantry housing is thereby possible. A further advantage is that the components in the gantry housing are very specific, and therefore can be extremely effectively cooled. The cooling system is thus overall relatively simple, cost-effective and efficient.

BRIEF DESCRIPTION OF THE DRAWINGS

The invention is explained in detail in the following using exemplary embodiments, with reference to attached Figures. Identical components are respectively provided with the same reference characters in the various Figures.

FIG. 2 is a schematic cross-section through the gantry housing of the computer tomography system according to FIG. 1 along the section line Q-Q';

FIG. 4 is a schematic cross-section through the gantry housing of a computer tomography system similar to FIG. 2, however with an inventive cooling system according to a second exemplary embodiment.

DETAILED DESCRIPTION OF THE PREFERRED EMBODIMENTS

Figure 1:
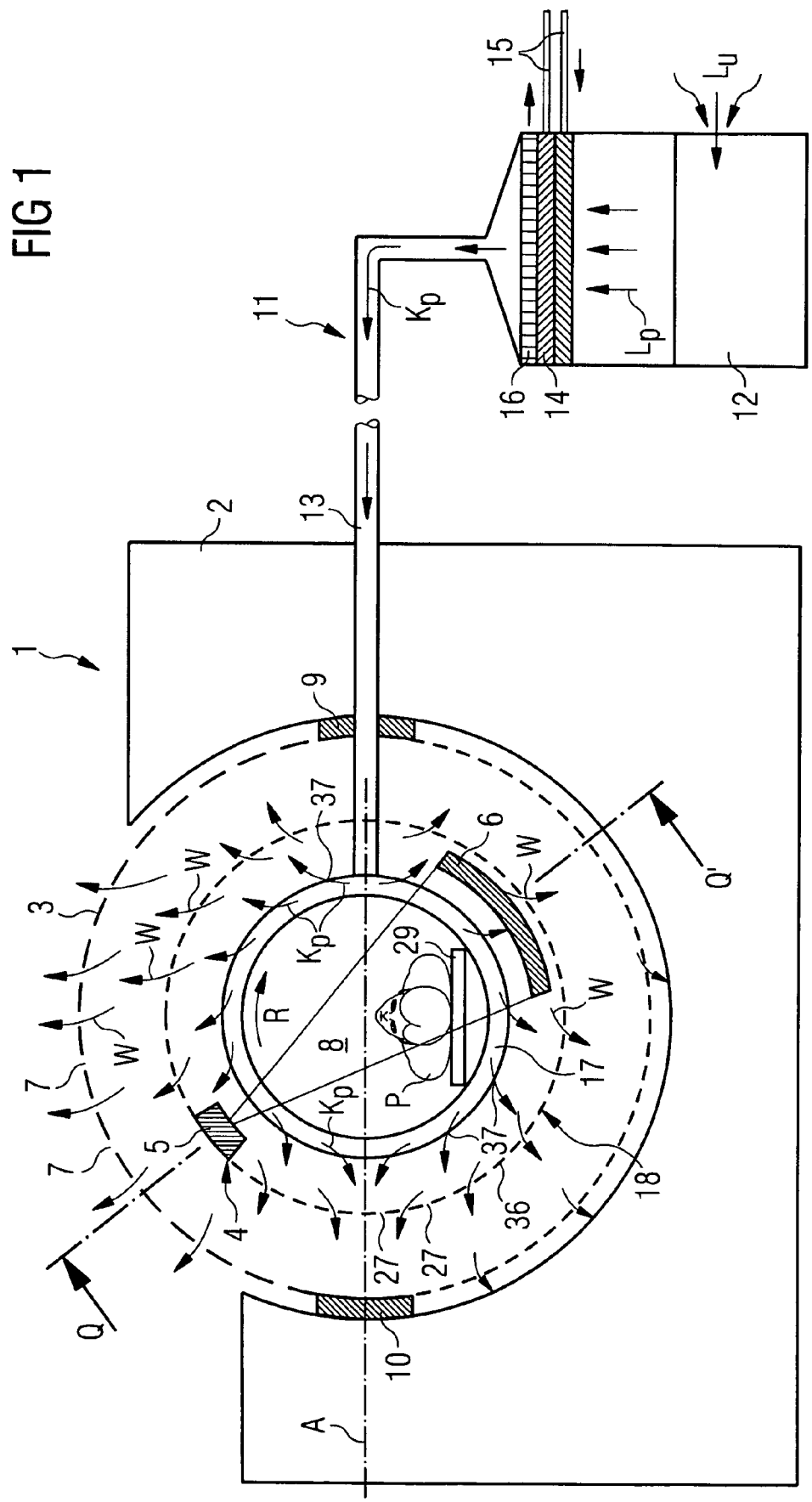
FIG. 1 is a schematic cross-section through a computer tomography system with an inventive cooling system according to a first exemplary embodiment.

According to aspects of the invention, compressed air is preferably compressed by a compressor to significantly more than atmospheric pressure. This compressor can be arranged in proximity to the computer tomography system, for example directly next to the tomography apparatus in a separate housing in the examination space, or can even be integrated in the stationary part of the computer tomography system. However, the compressor can also be housed in a separate technical space, for example in an equipment room, in order to prevent a possible disturbance in the examination space by the noise created in the operation of the compressor. To prepare the compressed air, the cooling system can also comprise connection means to connect to a compressed air system that already exists anyways in most clinics. However, the requirement for this is that the compressed air system must provide compressed air at a sufficiently high pressure and sufficiently high air flow rate. A very cost-effective realization would thus be given. In particular, no additional maintenance costs accrue.

Upon issuing from a nozzle, the compressed air expands very quickly, whereby the temperature of the air automatically drops. This thermodynamically advantageous property of cooling by means of compressed air is preferably further reinforced by providing additional cooling of the compressed air. For this, at least one heat exchanger is integrated into the cooling system in order to cool the compressed air before the feed to the components to be cooled—preferably cooling the compressed air below the ambient temperature. The heat exchanger is thereby preferably placed adjacent to the compressor and can be connected to a fluid cooling such as, for example, a simple water cooling apparatus.

The compressed and cooled air is preferably carried through heat-insulated lines from the compressor to the computer tomography system and into the gantry housing. An increase in the temperature of the compressed air is thus prevented and a higher degree of efficiency of the cooling system is maintained. It is especially advantageous if the feed lines are only of a small diameter, in order to keep the space requirement as small as possible.

In computer tomography systems of the previously cited type, the component that generates the main portion of the heat, i.e. the x-ray source, is connected, for example, in a carrier ring that is rotatable around a measurement space in the gantry housing. Further components that themselves generate heat, or must be protected from heating by the heat generated by the x-ray source, can also be attached in or on this carrier ring.

The inventive cooling system is fashioned according to a particularly preferred embodiment such that the compressed, possibly also, cooled air is directly conducted via the outlet openings to the components to be cooled, mounted in or on the carrier ring, that pass by upon rotation of the carrier ring.

In a variation, under formation of an angle profile running annularly around the rotation axis, such a carrier ring comprises an annularly rotating first surface extending essentially radially (meaning aligned at a right angle relative to the rotation axis of the carrier ring), as well as an annularly rotating second surface extending axially (meaning running parallel to the rotation axis), arranged on the radial outer end of the first surface. For reasons of simplicity, these surfaces will henceforth also be designated as a radial surface or, respectively, axial surface. However, the carrier ring can in principle also be fashioned in a different arbitrary manner, for example in the form of a simple tubular or pipe frame mount.

A variation of the invention provides that the exhaust element is realized as a nozzle ring, preferably arranged in a radial inner region of the gantry housing. The compressed air thereby issues from a number of openings or, respectively, nozzles that are preferably placed on the entire circumference of the nozzle ring, radially outwards from the measurement space in the direction of the carrier ring rotating past. The components attached in or on the carrier ring are hereby exposed to a strong cooled compressed air stream during the operation of the computer tomography system, and are thus effectively cooled. In order that the heated air flows away again from the components as efficiently as possible, in the design cited above of a carrier ring with an annular rotating angle profile, the axial surface of the carrier ring is provided with flow-through openings through which the heated air escapes.

In a further variant of the invention, a number of nozzle plates are installed as streaming elements at specific circumferential positions in the gantry housing or, as the case may be, flanged on the gantry housing.

In the design cited above of a carrier ring with an annularly rotating angle profile, the nozzle plates preferably lie close to the radial surface of the carrier ring provided with flow-through openings. The compressed air flows through the flow-through openings and hits the components to be cooled that are rotating past. The nozzle plates can be fashioned from one or more segments, such that only a part of the radial surface of the carrier ring is covered by the segments. However, the nozzle plate can also be fashioned such that the segments substantially cover the entire perpendicular surface of the carrier ring and form a complete ring.

A combination of both previously cited variants is typically also possible, meaning a design in which both a nozzle ring and one or, respectively, more nozzle plates are mounted in the gantry housing.

A further embodiment of the invention provides that stationary components arranged in the gantry housing are also specifically cooled with cooled compressed air. For this, the compressed air is conducted via preferably heat-insulated, individual air feed tubes or lines to nozzle heads that are located in direct proximity to the components to be cooled. The nozzle heads preferably comprise a number of exhaust openings or nozzles that are attached and aligned such that the compressed air streams directly onto the component to be cooled. A component can, depending on the requirement, be cooled by one or also by a plurality of nozzle heads.

In an open embodiment of the invention, the gantry housing is designed such that the outer wall of the gantry housing comprises exhaust openings. In this variant, the heated air escapes directly from the exhaust openings of the gantry housing into the examination space. The exhaust openings can be a larger opening. However, the housing is preferably perforated radially outwards (meaning away from the examination subject) in a specific region, particularly preferably along the entire circumference. In particular when the components are cooled with compressed air cooled in advance, a heating of the examination space or, respectively, a strain on the climate control system that is present due to the escaping heated air is not to be expected.

In an alternative closed system, the heated air is exhausted from the gantry housing via an exhaust device. For this, preferably at least one blower fan arranged in the stationary part is used. In most computer tomography systems, the gantry housing is positioned such that it can be pivoted around an axis by means of two coaxially (meaning arranged on the axis on two opposite sides on the gantry housing) arranged bearings on the stationary part of the computer tomography system. In such systems, the heated air is preferably sucked into the gantry foot in the region of one or both bearings. The required blowers are thereby particularly preferably located near the bearings.

The heated air can hereby flow out of the gantry housing and into the stationary part through a flow-through opening running lengthwise through the bearing. The bearing is, for example, fashioned as a bearing ring or a bearing tube for this. The clear opening diameter, meaning the inner diameter of the bearing ring or, respectively, of the bearing tube, should thereby be as large as possible so that the air exchange can ensue optimally unhindered. Alternatively, flow-through openings can be located in the opposite surfaces of the gantry housing and of the housing of the stationary part, adjacent to the bearing. The flow-through openings are thereby sealed outwards, such that no air can arrive in the patient examination space from the gap between gantry housing and the housing of the gantry foot. The possible shape, opening size and arrangement of the flow-through openings are optimally set by the housing geometry and the housing dimensions for each type series. Furthermore, a combination of both previously cited variants is also possible, i.e. a design in which flow-through openings are located within the bearings and in the housing surfaces next to the bearings.

The bearings are incidentally also particularly preferably used for an implementation of the cooled compressed air feed lines into the gantry housing.

In order to prevent the formation of water vapor in the gantry housing due to the heat generated in the operation of the computer tomography system, a dehumidifier is installed in the cooling system in a particularly advantageous exemplary embodiment. The dehumidifier is preferably located in immediate proximity to the compressor, in particular behind the compressor.

In spite of the space and cost-saving design, due to its high efficiency the inventive cooling system is sufficient for a cooling of all components located in the gantry housing. Moreover, however, it can also be used supplementary to already known cooling methods. The compressed air cooling can in principle also be used in order to cool mutually rotating heat exchangers arranged on the gantry, and therewith to increase their degree of efficiency. In particular, a retrofitting of already existing computer tomography systems is also possible. Only a suitable arrangement of compressed air supply lines and streaming elements on and/or in the gantry housing are necessary for this.

With reference to the drawings, the computer tomography system 1 shown in FIG. 1 comprises as a primary component a stationary part 2 (also called a gantry foot 2 in the following) and a gantry housing 3 movable thereon. The gantry housing 3 is thereby positioned such that it can be pivoted on an axis A by means of two coaxial bearings 9 and 10 on two opposite sides on the stationary part 2 of the computer tomography system 1. Located in the gantry housing 3 is a gantry 4, that is rotatable in the rotation direction R, on which an x-ray source and a detector 6 are arranged opposite one another. In the operation of the computer tomograph 1, the gantry 4 rotates around the examination subject (shown here as a patient P) positioned in the examination space 8 on a bed 29, whereby a fan-shaped x-ray originating from the x-ray source 5 permeates the examination subject P and impinges on the detector 6. A slice image of the inside of the examination subject P is thus acquired in a slice lying in the rotation plane.

In order to cool the various components of the gantry, in particular the x-ray source 5, the computer tomography system 1 inventively comprises a special cooled compressed air feed device 11 which works with cooled compressed air.

This cooled compressed air feed device 11 comprises a compressor 12 which is arranged outside of the computer tomography system 1 in a separate housing. The compressor 12 admits ambient air $L_u$ and compresses it to significantly more than atmospheric pressure.

In the compressor housing, which is downstream from the actual compressor 12, a heat exchanger 14 is arranged that is connected via a cooling water lines 15 to an external cooling device that cools the compressed ambient air $L_p$ to significantly below ambient temperature. The compressed, cooled air $K_p$ (also called cooled compressed air $K_p$) is additionally dehumidified by means of a dehumidifier 16.

The cooled compressed air $K_p$ is guided into the gantry housing 3 via heat-insulated cooled compressed air lines 13. The feed from the stationary part 2 of the computer tomography system 1 into the gantry housing 3 here ensues via one of the bearings 9. In the gantry housing 3, the cooled compressed air $K_p$ flows into a nozzle ring 17 which comprises along its entire circumference exhaust openings 37 (called nozzles 37 in the following) that are directed radially outwards.

FIG. 2 shows a cross-section along the section line Q-Q' through the gantry housing 3 of the computer tomography system 1 according to FIG. 1.

The carrier ring 18 here comprises an angle profile that annularly rotates around the rotation axis of the gantry 4, with an annularly rotating first surface 35 extending substantially radially (meaning aligned at a right angle relative to the rotation axis), and an annularly rotating second surface 36 extending axially (meaning arranged parallel to the rotation axis) on the radially outward end of the first surface 35. This means the carrier ring 18 exhibits an essentially right-angle profile in cross section. The individual components 5 and 6 of the gantry 4 are hereby suspended within the angle profile of the carrier ring 18.

The cooled compressed air $K_p$ flows through the nozzle 37 of the nozzle ring 17 onto the components 5 and 6 as they rotate past one another, the nozzle ring 17 being mounted in the carrier ring 18. Alternately, the air flows through the flow-through openings 27 arranged in the axial second surface 26 of the carrier ring 18 past the components 5 and 6. The heated air W can subsequently escape outwards via exhaust openings 7 in the gantry housing 3.

A further component 26, for example an electrical circuit that is mounted stationary in the gantry housing 3, is specifically cooled with cooled compressed air $K_p$ that is blown through a nozzle head 25 directly onto the component 26 to be cooled. This nozzle head 25 comprises a plurality of lateral nozzles. The heated air W again escapes through the exhaust openings 7 in the gantry housing 3.

Figure 3:
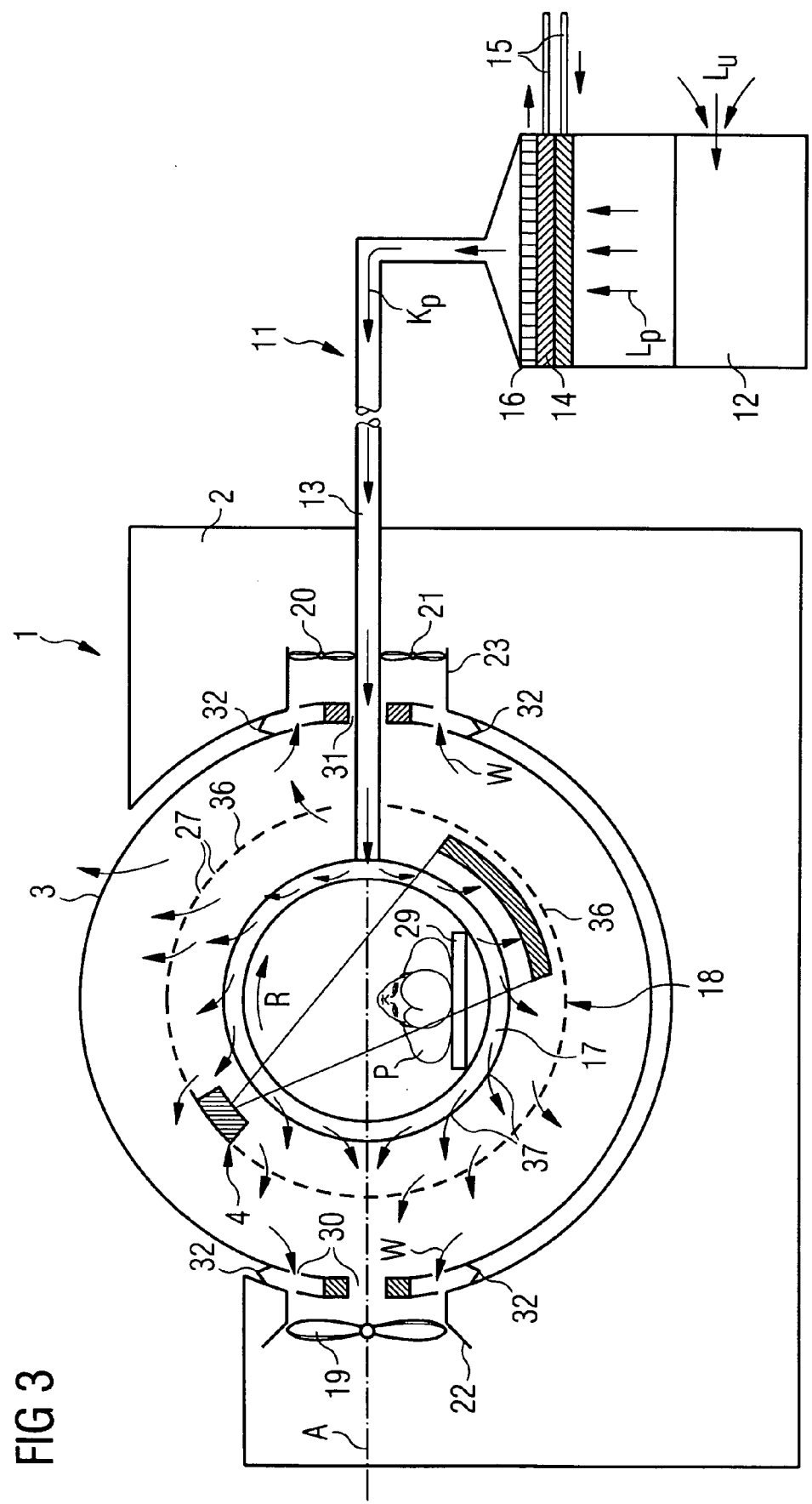
FIG. 3 is a schematic cross-section through a computer tomography system with an inventive cooling system according to a second exemplary embodiment.

FIG. 3 shows an exemplary embodiment fashioned similar to FIG. 1. However, here the heated air is sucked into the housing of the gantry foot 2 instead of escaping into the surroundings through openings in the gantry housing 3. For this, respective flow-through openings 30 and 31 are located in the bearings 9 and 10 on which the gantry housing 3 can be pivoted on the stationary part 2, and in the opposite surfaces in the housing of the gantry foot 2 and in the gantry housing 3 in the region of the bearings 9 and 10. Annularly circumferential seals 32 are arranged around the flow-through openings 30 and 31 between the gantry housing 3 and the housing of the stationary part 2, so that the air to be dissipated can not arrive in the examination space. The heated air W is thereby exhausted from the gantry housing 3 by blowers 19, 20 and 21 via guide funnels 22 and 23 and discharged (not shown) from the examination space.

The previously specified arrangements of the blowers 19, 20 and 21 are thereby the be understood only exemplarily.

Thus, for example, the blowers can be arranged depending upon requirement in the gantry foot 3 or outside of the gantry foot 3.

FIG. 4 again shows a cross section through the gantry housing 3 of a computer tomography system 1 similar to FIG. 2. However, in this exemplary embodiment, streaming elements are installed in the gantry housing at various circumferential positions in the form of nozzle plates 24. These nozzle plates 24 comprise exhaust openings or, respectively, nozzles 33 on their side facing the carrier ring. The feed to the nozzle plates 24 ensues, for example, via a ring line (not shown). The compressed, cooled air $K_p$ flows from the nozzles 33 and further through flow-through openings 28 mounted in the radial surface 35 of the carrier ring 18, and is thus blown on the gantry components 5 and 6 rotating past with the carrier ring 18. The nozzle plates 24 thereby lie close to the surface 35 of the carrier ring 18 provided with flow-through openings. In this exemplary embodiment, as needed the axial surface 36 of the carrier ring 18 could also be provided with flow-through openings.

As FIG. 4 shows, a further stationary component 26 in the gantry housing 3 is directly cooled with the aid of a separate nozzle head 34, that here comprises a single nozzle at its end.

The heated air W is exhausted from the gantry housing 3 in this exemplary embodiment according to FIG. 3. However, it is also possible in this exemplary embodiment that the heated air W escapes from the gantry housing 3 through exhaust openings 7, as in the exemplary embodiment according to FIG. 1.

Finally, it is again to be noted that the previously specified cooling system are only exemplary embodiments that can be modified by the average man skilled in the art within the framework of the invention. Thus, for example, the cooling system can also be used in a non-rotating gantry. The design of the carrier ring can also ensue according to arbitrarily different specifications, for example as an open tubular frame mount. In this case, the cooled compressed air can arrive at the components to be cooled via the open mount, and the heated air can further escape through the mount. The carrier ring can also be fashioned to be rigid, for example in the form of an annular track or rail on which the gantry rotates around the examination subject. The cooling system can be used exactly the same for such gantry designs. The arrangement of the streaming elements can also ensue depending upon requirements. Thus, for example, the nozzle plates can be flanged outwards on the gantry housing. The entire radial circumference of the gantry housing, or also just a partial circumference, can thereby be covered. The cooled compressed air feed lines can in this case be individually mounted outwards on the nozzle plates.

Although other modifications and changes may be suggested by those skilled in the art, it is the intention of the inventors to embody within the patent warranted hereon all changes and modifications as reasonably and properly come within the scope of their contribution to the art.

I claim:

1. A cooling system for components of a computer tomography system arranged in a gantry housing, comprising:
    a cooled air feed device including:
        an air compressor operable to compress air; and
        streaming elements connected to receive the compressed air from said air compressor and disposed and formed such that the compressed air flows onto the components to be cooled,
    an annular carrier ring in or on which at least one of the components to be cooled is arranged, said annular carrier ring being rotatable around a measurement space in the gantry housing; and
    at least one exhaust element mounted stationarily and disposed in or on the gantry housing through which the compressed air flows onto the components passing said at least one exhaust element upon a rotation of the carrier ring.

2. A cooling system according to claim 1, wherein said air compressor is one of disposed in the computer tomography system and adjacent to the computer tomography system, said air compressor being operable to accept and compress ambient air.

3. A cooling system according to claim 1, further comprising:
    a cooling device connected to receive the compressed air to cool the compressed air.

4. A cooling system according to claim 1, further comprising:
    lines connected between said air compressor and said streaming elements to conduct the compressed air to said streaming elements; and
    heat insulation at least along sections of said lines.

5. A cooling system according to claim 1, wherein said at least one exhaust element is a nozzle ring.

6. A cooling system according to claim 5, wherein said nozzle ring is arranged in a radial inner region of the gantry housing such that the compressed air flows substantially radially outwards onto the components to be cooled that are in or on said carrier ring.

7. A cooling system according to claim 1, further comprising:
    a plurality of nozzle plates arranged at predetermined circumferential positions in or on the gantry housing.

8. A cooling system according to claim 7, wherein said carrier ring, under formation of an angle profile running annularly around a rotation axis, includes
    an annularly rotating first surface with flow-through openings; and
    an axially extending annularly rotating second surface arranged on a radially outer end of said first surface;
    said nozzle plate being arranged in the gantry housing such that said first surface of said carrier ring passes close to said nozzle plates upon rotation such that the compressed air flows through the flow-through openings onto the components to be cooled arranged in said carrier ring.

9. A cooling system according to claim 1, further comprising:
    a second surface of said carrier ring defining flow-through openings through which heated air escapes essentially radially outwards from said carrier ring into the gantry housing.

10. A cooling system according to claim 1, further comprising:
    nozzle heads arranged and fashioned such that the compressed air is guided directly to stationarily arranged components inside the gantry housing.

11. A cooling system according to claim 1, wherein said gantry housing defines exhaust openings through which heated air escapes outwards.

12. A cooling system according to claim 1, further comprising:
    an exhaust device operable to draw heated air from the gantry housing.

13. A cooling system according to claim 12, wherein said exhaust device includes at least one blower.

14. A cooling system according to claim 1, further comprising:
a dehumidifier upstream from said streaming elements.

15. A cooling system for components of a computer tomography system arranged in a gantry housing, comprising:
a cooled air feed device including:
an air compressor operable to compress air; and
streaming elements connected to receive the compressed air from said air compressor and disposed and formed such that the compressed air flows onto the components to be cooled;
an exhaust device operable to draw heated air from the gantry housing, said exhaust device including at least one blower;
two coaxial bearings on two opposite sides on a stationary part of the computer tomography system by which the gantry housing is positioned around an axis, the cooling system being fashioned such that the heated air in a region of at least one of the bearings is guided out of the gantry housing in the stationary part.

* * * * *